United States Patent Office

Re. 25,205
Reissued July 24, 1962

25,205

SILICONE COMPOSITION FOR THE RELIEF OF GASTRO-INTESTINAL DISTRESS AND METHOD OF USING SAME

Wolffe Harry Feinstone, Memphis, Tenn., assignor, by mesne assignments, to Plough Laboratories, Inc., Memphis, Tenn., a corporation of Tennessee No Drawing. Original No. 2,951,011, dated Aug. 30, 1960, Ser. No. 628,576, Dec. 17, 1956. Application for reissue June 12, 1961, Ser. No. 116,926
6 Claims. (Cl. 167—55)

Matter enclosed in heavy brackets [ ] appears in the original patent but forms no part of this reissue specification; matter printed in italics indicates the additions made by reissue.

This application is a continuation-in-part of application Serial No. 395,847, filed December 2, 1953, now abandoned.

This invention relates to a therapeutic composition for oral administration, and more particularly to a composition whereby the walls of the alimentary tract are protected against irritation and erosion.

One of the objects of this invention is to provide a particulate therapeutic composition, the individual particles of which carry a wall protecting material.

Another object is to provide such a composition in which the protective coating material serves to relieve flatulence.

Still other objects will become apparent to those skilled in the art in the light of the following description.

In accordance with this invention, generally stated, a therapeutic composition is provided in dry, particulate form, the individual particles of which are coated with one of the organo-silicon oxide polymers (or organopolysiloxanes), more popularly known as silicones.

The organopolysiloxanes are generally insoluble, jelly-like or fluent substances, not miscible with body fluids. Their administration, plain, deposits in the stomach a relatively compact mass in a small area, whence it is passed through the intestinal tract, substantially without dispersion, and substantially without effect. They have been suggested as enteric coatings, and as such may be more thoroughly dispersed in the intestinal tract. However, their use as enteric coatings has not been satisfactory ("Drug Standards," vol. 24, No. 1, pp. 19–21), and the amount of organopolysiloxane which can be carried on the surface of a tablet, relative to the volume of material in the tablet, without completely preventing disintegration of the tablet, is so small as to give no effective protection to the walls of the gastro-intestinal tract, and to exert no appreciable anti-flatulent effect.

I have discovered that, if an organopolysiloxane is intimately mixed with a suitable carrier, so that small amounts of the organopolysiloxane are gathered upon and supported by the individual particles of the carrier, then, upon internal administration of the mixture, the supporting particles will be widely dispersed against the walls of the alimentary tract, carrying with them the supported organopolysiloxane. Now, if the supporting substance is of such character that it is dissolved, disintegrated or decomposed within the gastro-intestinal tract, or any selected portion thereof, the organopolysiloxane particles, being chemically and mechanically unaffected within the tract, will be deposited, in such widely dispersed condition, upon the walls of the tract. In the appended claims, the word "disintegrated" is used to encompass dissolution and decomposition. It will be observed that when the silicone-coated particles stick to the surface of the gastro-intestinal wall, the wall is protected at the precise point at which the erosive or irritant effect of the medicament is likely to be greatest, since the concentration of the solution formed when the particle is dissolved is greatest at the immediate locus of the particle. Actually, the particulate material is generally well distributed over the surface of the area of the gastro-intestinal tract in which the material distintegrates. As a consequence, and in part because of the recognized capacity of the organopolysiloxanes to resist attack by substances present in the gastro-intestinal tract, the walls of that tract (or of such selected portion or portions thereof) will be provided with a coating which not only provides the mechanically protective effect above-mentioned, but also will introduce, at those locations, a defoaming action. Even if the supporting substance is not so attacked, at least some of the supported organopolysiloxane will be deposited, in wide dispersion, upon the tract walls.

I have found that the organopolysiloxanes may effectively be supported in the manner above-described upon many non-toxic substances. For the alleviation of hyperacidity, or even of the discomfort resulting from the normal acid condition of gastro-intestinal fluids in the presence of an ulcerous condition, it is conventional to administer substances known as gastric antacids, including aluminum hydroxide, magnesium carbonate, magnesium trisilicate, sodium bicarbonate, calcium caseinate, magnesium oxide, calcium carbonate, sodium carboxymethylcellulose, aluminum aminoacetate, calcium phosphate, aluminum trisilicate, magnesium phosphate, bismuth subcarbonate, aluminum phosphate, dihydroxy aluminum aminoacetate and potassium phosphate. Any of these substances may be effectively used as carriers for the organopolysiloxanes in the preparation of a composition according to the present invention. The solid carrier, in a finely-divided state, is intimately mixed, in accordance with conventional pharmaceutical practice, with the selected organopolysiloxane, to the end that each particle of the carrier shall be, in effect, "coated" with the organopolysiloxane. Preferably, the proportions of the ingredients will be such that the ultimate mixture remains discrete and fluent, and of granular character suitable for direct administration or for compression to tablet form. Such a mixture may then be compressed into tablet form, with or without therapeutically inert filler materials such as cane sugar, milk sugar, starch, talc, or the like, and with or without suitable, non-toxic, binder substances. The preferred range of organopolysiloxane is between .5% and 50% of the weight of the dry particulate material.

As will be apparent from the above discussion, desirable and beneficial results can be attained from the administration of an organopolysiloxane similarly carried upon other types of carriers, including carriers which have no therapeutic effect. Thus, a selected organopolysiloxane might be intimately mixed with talc, starch or the like alone, and then compressed into tablet dosage form or dispersed in a suitable liquid vehicle. The protective coating effect and the anti-flatulence effect can thereby be attained, if other medication, concurrently, is not required.

I have found, further, that one of the organopolysiloxanes may similarly be administered in intimate mixture with an anion exchange resin such as, for instance, polyethylene polyamine methylene substituted resin of diphenylol dimethylmethane and formaldehyde in basic form, to provide an antacid effect along with the coating and anti-foaming effects.

It may, on occasion, be desirable to employ, along with the organopolysiloxane, forms of intestinal medication other than antacid substances, such, for instance, as atropine or its substantial therapeutic equivalent, non-absorbable sulfonamides, adsorbents, and so forth. A selected one of the organopolysiloxanes may be, to that end, analogously intimately mixed with the selected medicament for administration in the manner above outlined. Broadly stated, it may be said that my invention contemplates the administration of an organopolysiloxane dispersed with any non-toxic solid which is capable of mechanically supporting the organopolysiloxane in widely-dispersed condition, and which is capable of transferring at least some of the supported organopolysiloxane to the walls of the alimentary tract (or some selected portion thereof) through mechanical action or through being digested, dissolved, distingrated or decomposed in the presence of fluids to be found in the alimentary tract.

Of course, the compositions, as above-described, may be prepared in widely varying proportions and may be extended with any desired excipient, including the sugars, water, starch, flavoring agents, coloring agents, preservatives, talc, stearates, and the like.

The organopolysiloxanes preferably selected for use in the composition are represented by the following formulae:

$$[R_xSiO_{(4-x)/2}]_n$$

where x is a small whole number; n=1 to 2000; and R is an organic radical; or

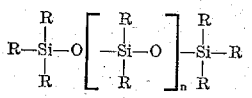

where R is a [$cH_3$] $CH_3$ or other organic radical and n=0 to 2000.

In general, the essential ingredients of the composition of my invention will be combined in proportions within the broad range as follows, though in certain specific instances, the proportions may vary still further:

| | | |
|---|---|---|
| Antacid | gm | 0.1–1.0 |
| Organpolysiloxane | mg | 10–100 |

*This range is inherently and by simple arithmetic from 1% (10:1000 mg.) to 100% (100:100 mg.) organopolysiloxane to carrier.*

[That is to say, as] *As* is indicated in the specific examples hereafter set out, the optimum range of proportions of organopolysiloxane to antacid by weight, is between 1% and 10% of organopolysiloxane.

Some specific examples of the ingredients and the proportions thereof, in antacid-organopolysiloxane compositions, are given below; but it is to be understood that these are intended to be illustrative and not limitative:

EXAMPLE 1

| | | |
|---|---|---|
| Sodium carboxymethylcellulose | gm | 0.3 |
| Magnesium trisilicate | gm | 0.2 |
| Methyl polysiloxane | mg | 10–25 |
| (DC Antifoam A) | | |

EXAMPLE 2

| | | |
|---|---|---|
| Calcium caseinate | gm | 0.8 |
| Calcium carbonate | gm | 0.2 |
| Methyl polysiloxane | mg | 10–25 |

EXAMPLE 3

| | | |
|---|---|---|
| Polyamine-methylene resin | gm | 0.25 |
| Dimethyl polysiloxane | mg | 10–25 |

EXAMPLE 4

| | | |
|---|---|---|
| Polyamine-methylene resin | | 0.25 |
| Methyl polysiloxane | mg | 10–25 |

EXAMPLE 5

| | | |
|---|---|---|
| Dihydroxy aluminum aminoacetate | gm | 0.5 |
| Methyl polysiloxane | mg | 10–25 |

EXAMPLE 6

| | | |
|---|---|---|
| Magnesium trisilicate | gm | 0.5 |
| Aluminum hydroxide gel | gm | 0.25 |
| Methyl polysiloxane | mg | 10–25 |

EXAMPLE 7

| | | |
|---|---|---|
| Bismuth subcarbonate | gm | 0.5 |
| Calcium phosphate, tribasic | gm | 0.5 |
| Kaolin | gm | 2.0 |
| Pectin | gm | 0.26 |
| Phthalylsulfacetamide | gm | 1.0 |
| Belladonna, tincture | cc | 0.6 |
| Dimethyl polysiloxane | mg | 50–200 |

EXAMPLE 8

| | | |
|---|---|---|
| Sodium bicarbonate | gm | 0.275 |
| Calcium carbonate | gm | 0.15 |
| Magnesium carbonate | gm | 0.1 |
| Magnesium trisilicate | gm | 0.07 |
| Bismuth subcarbonate | gm | 0.002 |
| Methyl polysiloxane | mg | 10–25 |

Having thus described my invention, what is claimed and desired to be secured by Letters Patent is:

1. A therapeutic composition comprising particulate, granular, disintegrable antacid material, the particles of which are coated with a non-toxic organopolysiloxane, said organopolysiloxane being present in an amount between 1% and 10% of the weight of the dry granular material, said composition containing 10 to 200 milligrams of said organopolysiloxane per dosage unit, being sufficient to coat said particles and to exert a wall protective and anti-flatulent effect upon the gastro-intestinal system but to leave said particles discrete and fluent.

*2. The composition of claim 1 in liquid dosage form.*

*3* [2]. A method of treating gastro-intestinal distress, which consists of administering orally to a human patient a composition comprising a particulate carrier coated with a non-toxic organopolysiloxane, said organopolysiloxane being present in the amount of 1% to 50% by weight of said carrier, said composition containing 10 to 200 milligrams of said organopolysiloxane per dosage unit.

*4* [3]. The method of claim [2] *3* wherein the composition is administered in tablet form.

*5. A method of treating gastro-intestinal distress, which consists of administering orally to a human patient a composition comprising a particulate carrier supporting a non-toxic organopolysiloxane, said organopolysiloxane being present in the amount of 1% to 100% by weight of said carrier, said composition containing 10 to 200 milligrams of said organopolysiloxane per dosage unit.*

*6. The method of claim 5 wherein the composition is administered in liquid dosage form.*

References Cited in the file of this patent or the original patent

UNITED STATES PATENTS

| | | |
|---|---|---|
| 2,394,107 | Roseman | Feb. 5, 1946 |
| 2,474,704 | Thayer | June 28, 1949 |
| 2,512,192 | Yen | June 20, 1950 |

OTHER REFERENCES

Hammarlund: J.A.P.A. (Sci. Ed.), vol. 41, No. 6, June 1952, pp. 295–298.

Barondes: The Military Surgeon, vol. 106, No. 5, May 1950, pp. 379–387, part. pp. 379, 381 and 384–386.

Nickerson: Fed. Proc., vol. 12, No. 1168, 1953, pp. 354–355.

McGregor: Silicones in Med. and Surgery, 1957, p. 27.